United States Patent
Fedorova et al.

(10) Patent No.: US 9,745,629 B2
(45) Date of Patent: Aug. 29, 2017

(54) IN VITRO METHOD FOR SCREENING FOR CANDIDATE COMPOUNDS FOR PREVENTING AND/OR ATTENUATING AGEING OF THE SKIN, AND/OR FOR HYDRATING THE SKIN

(71) Applicant: CHANEL PARFUMS BEAUTE, Neuilly sur Seine (FR)

(72) Inventors: Elena Fedorova, Whippany, NJ (US); Christelle Lasserre, Jersey City, NJ (US)

(73) Assignee: CHANEL PARFUMS BEAUTE, Neuille sur Seine (FR)

(*) Notice: Subject to any disclaimer, the term of this patent is extended or adjusted under 35 U.S.C. 154(b) by 0 days.

(21) Appl. No.: 15/196,393

(22) Filed: Jun. 29, 2016

(65) Prior Publication Data
US 2016/0304955 A1 Oct. 20, 2016

Related U.S. Application Data

(62) Division of application No. 14/115,700, filed as application No. PCT/EP2012/059064 on May 15, 2012.

(60) Provisional application No. 61/486,854, filed on May 17, 2011.

(51) Int. Cl.
| | | |
|---|---|---|
| C12Q 1/68 | (2006.01) |
| G01N 33/50 | (2006.01) |
| G01N 33/68 | (2006.01) |
| A61K 8/34 | (2006.01) |
| A61Q 19/00 | (2006.01) |
| A61Q 19/08 | (2006.01) |
| A61K 8/06 | (2006.01) |
| A61K 8/73 | (2006.01) |
| A61K 8/81 | (2006.01) |
| A61K 8/92 | (2006.01) |

(52) U.S. Cl.
CPC .......... *C12Q 1/6876* (2013.01); *A61K 8/062* (2013.01); *A61K 8/345* (2013.01); *A61K 8/347* (2013.01); *A61K 8/735* (2013.01); *A61K 8/8152* (2013.01); *A61K 8/92* (2013.01); *A61Q 19/004* (2013.01); *A61Q 19/007* (2013.01); *A61Q 19/08* (2013.01); *C12Y 208/02* (2013.01); *G01N 33/5023* (2013.01); *G01N 33/5044* (2013.01); *G01N 33/6881* (2013.01); *A61K 2800/78* (2013.01); *C12Q 2600/148* (2013.01); *C12Q 2600/158* (2013.01); *G01N 2333/91194* (2013.01); *G01N 2800/20* (2013.01)

(58) Field of Classification Search
None
See application file for complete search history.

(56) References Cited

U.S. PATENT DOCUMENTS

| | | | |
|---|---|---|---|
| 5,955,083 A | 9/1999 | Bonte et al. | |
| 2004/0048785 A1 | 3/2004 | Dalko et al. | |
| 2009/0324752 A1 | 12/2009 | Lasserre et al. | |
| 2010/0159045 A1 | 6/2010 | Lasserre et al. | |
| 2011/0262025 A1* | 10/2011 | Jarrold ................ | A61K 8/606 382/133 |

FOREIGN PATENT DOCUMENTS

WO 2011069913 6/2011

OTHER PUBLICATIONS

Ndiaye (Archives of Biochemistry and Biophysics vol. 508 (Jan. 4, 2011) pp. 164-170).*
Ndiaye et al., "The grape antioxidant resveratrol for skin disorders: Promise, prospects, and challenges", Archives of Biochemistry and Biophysics, vol. 508, Jan. 4, 2011, pp. 164-170.
E. Fedorova et al.; "Expression of Human Epidermal "Glycogenes" in skin cells after UVB irradiation and their modulation with active ingredients"; Journal of Investigative Dermatology; vol. 132; May 2012; XP002678784.

* cited by examiner

*Primary Examiner* — Amanda Haney
(74) *Attorney, Agent, or Firm* — Young & Thompson

(57) ABSTRACT

The identification and the use of compounds which activate the expression of at least one gene selected from LARGE, HS6ST2 and ST8SIA1 is provided. An in vitro method for screening for candidate compounds includes:
(a) bringing at least one test compound in contact with a sample of keratinocytes in vitro;
(b) measuring the expression of at least one gene selected from LARGE, HS6ST2 and ST8SIA1, in the keratinocytes; and
(c) selecting the compounds for which an activation of at least 1.4 fold of the expression of at least one of the LARGE, HS6ST2 and ST8SIA1 genes is measured in the keratinocytes treated in (a) compared with the untreated keratinocytes.

The candidate compounds may be useful for preventing and/or attenuating ageing, and/or for hydrating skin.

28 Claims, No Drawings

IN VITRO METHOD FOR SCREENING FOR CANDIDATE COMPOUNDS FOR PREVENTING AND/OR ATTENUATING AGEING OF THE SKIN, AND/OR FOR HYDRATING THE SKIN

FIELD OF THE INVENTION

The invention relates to the identification and the use of compounds which activate the expression of at least one gene selected from LARGE, HS6ST2 and ST8SIA1, for preventing and/or attenuating ageing, particularly photoageing, and/or for hydrating skin.

BACKGROUND

Genes encoding proteins involved in post-translational modifications, particularly in glycan synthesis, comprise glycosyltransferases and sulfotransferases, and are essential for regulating cell communications and activities. Glycan synthesis and modification enzymes encoded by the LARGE, ST8SIA1 and HS6ST2 genes are resident of the Golgi apparatus.

Precisely, LARGE gene encodes the N-acetylglycosaminyl transferase that is involved in glycosylation of alpha-dystroglycan ($\alpha$-DG) (Hewitt J E. Investigating the functions of LARGE: lessons from mutant mice. Methods Enzymol 2010: 479: 367-386, Hewitt J E. Abnormal glycosylation of dystroglycan in human genetic disease. Biochim Biophys Acta 2009: 1792: 853-861).

$\alpha$-DG is a major non-integrin adhesion molecule expressed at the interface between the basement membrane and the cell membrane, which links cytoskeletal actin to extracellular matrix and is likely involved in adhesion and regulation of signalling pathways (Ibraghimov-Beskrovnaya O. Ervasti J M, Leveille C J, Slaughter C A, Sernett S W, Campbell K P. Primary structure of dystrophin-associated glycoproteins linking dystrophin to the extracellular matrix. Nature 1992: 355: 696-702, Barresi R, Campbell K P. Dystroglycan: from biosynthesis to pathogenesis of human disease. J Cell Sci 2006: 119: 199-207). $\alpha$-DG requires extensive posttranslational processing in order to function as an extracellular matrix receptor (Yoshida-Moriguchi T, Yu L, Stalnaker S H, et al. O-mannosyl phosphorylation of alpha-dystroglycan is required for laminin binding. Science 2010: 327: 88-92). $\alpha$-DG has been implicated in several cell functions, such as growth control, cytoskeletal organization that may lead to cellular internal and external tension, cell polarization, differentiation and movement (Sgambato A, Caredda E, Leocata P, et al. Expression of alpha-dystroglycan correlates with tumour grade and predicts survival in oral squamous cell carcinoma. Pathology 2010: 42: 248-254).

$\alpha$-DG is expressed in epithelial cells and essential for epithelial development. Deficiency of perlecan, a major ligand of $\alpha$-DG, enhances shedding of $\alpha$-DG, destabilizes epithelial DG complex, and makes it accessible to proteolytic processing (Herzog C, Has C, Franzke C W, et al. Dystroglycan in skin and cutaneous cells: beta-subunit is shed from the cell surface. J Invest Dermatol 2004: 122: 1372-13 80).

The human LARGE gene is required for the generation of functional $\alpha$-DG and ligand binding activity of $\alpha$-DG (Yoshida-Moriguchi T, Yu L, Stalnaker S H, et al. O-mannosyl phosphorylation of alpha-dystroglycan is required for laminin binding. Science 2010: 327: 88-92).

Abnormal glycosylation of $\alpha$-DG disrupts binding to laminin and other proteins of the extracellular matrix resulting in diseases termed dystroglycanopathies (Moore C J, Goh H T, Hewitt J E. Genes required for functional glycosylation of dystroglycan are conserved in zebrafish. Genomics 2008: 92: 159-167; Martin P T. Congenital muscular dystrophies involving the O-mannose pathway. Curr Mol Med 2007: 7: 417-425; Moore C J, Hewitt J E. Dystroglycan glycosylation and muscular dystrophy. Glycoconj J 2009: 26: 349-357). The dystroglycanopathies show clinical phenotypes (in particular, muscular dystrophy, CNS abnormalities, and eye defects) that are presumed to be primarily due to this deficiency in $\alpha$-DG glycosylation. Inactivating mutations of LARGE also reduce the functional glycosylation of $\alpha$-DG and lead to dystroglycanopathies in mouse and humans. Mutations in the human LARGE gene are the basis of the dystroglycanopathy termed MDC1D (Longman C, Brockington M, Torelli S, et al. Mutations in the human LARGE gene cause MDC1D, a novel form of congenital muscular dystrophy with severe mental retardation and abnormal glycosylation of alpha-dystroglycan. Hum Mol Genet 2003: 12: 2853-2861). The mouse LARGE ortholog is 97.8% identical to human LARGE, and a deletion in mouse LARGE is the basis of the myd mouse that develops a muscular dystrophy similar to MDC1D.

Overexpression of LARGE in cultured fibroblasts from patients with different dystroglycanopathies generates functional $\alpha$-DG. In mutant CHO cells in which transfer of galactose, fucose or sialic acid to glycoconjugates is compromised, LARGE was able to induce $\alpha$-DG glycosylation. In cells carrying loss of function mutations in other genes in this pathway such as POMT1 or POMGnT1, overexpression of LARGE can induce glycosylation on $\alpha$-DG. Upregulation of LARGE is considered as therapeutic strategy for dystroglycanopathies that can rescue $\alpha$-DG glycosylation and function.

Like the LARGE gene, the ST8SIA1 gene encodes for a type II transmembrane protein involved in the synthesis of gangliosides. The HS6ST2 gene encodes an enzyme catalyzing the transfer of sulphate to heparan sulphate.

It is thus desirable and important to provide products or active agents which prevent, reduce or even inhibit the cellular senescence, particularly the keratinocyte senescence, more particularly UV-induced cell senescence.

The present invention thus provides a method for identifying such useful agents.

SUMMARY OF THE INVENTION

The present invention thus relates to an in vitro method for screening for candidate compounds for preventing and/or attenuating ageing of the skin, and/or for hydrating the skin, comprising the following steps:
 a. bringing at least one test compound in contact with a sample of keratinocytes;
 b. measuring the expression of at least one gene selected from LARGE, HS6ST2 and ST8SIA1, in said keratinocytes;
 c. selecting the compounds for which an activation of at least 1.4 fold of the expression of at least one of said genes is measured in the keratinocytes treated in a. compared with the untreated keratinocytes.

In one preferred embodiment, the present invention relates to an in vitro method for screening for candidate compounds for preventing and/or attenuating ageing of the skin, and/or for hydrating the skin, comprising the following steps:

a. bringing at least one test compound in contact with a sample of keratinocytes;
b. measuring the expression of at least one gene selected from LARGE, HS6ST2 and ST8SIA1, in said keratinocytes;
c. selecting the compounds for which an activation of at least 1.6 fold of the expression of at least one of said genes is measured in the keratinocytes treated in a. compared with the untreated keratinocytes.

According to a first embodiment, step b. is performed before and after step a. In this case, the expression of at least one gene selected from LARGE, HS6ST2 and ST8SIA1, measured in the keratinocytes before step a. corresponds to the control value (i.e. untreated keratinocytes).

Thus, step c. comprises the selection of the compounds for which an activation of at least 1.4 fold of the expression of at least one gene selected from LARGE, HS6ST2 and ST8SIA1 is measured in the keratinocytes treated in a. compared with the same keratinocytes before step a.

In one preferred embodiment, step c. comprises the selection of the compounds for which an activation of at least 1.6 fold of the expression of at least one gene selected from LARGE, HS6ST2 and ST8SIA1 is measured in the keratinocytes treated in a. compared with the same keratinocytes before step a.

According to another embodiment, the method comprises a first step a'. of preparing samples of keratinocytes. Thus, preferably, the present invention relates to an in vitro method for screening for candidate compounds for preventing and/or attenuating ageing of the skin, and/or for hydrating the skin, comprising the following steps:
a'. preparing at least two samples of keratinocytes;
a. bringing one of the samples into contact with at least one test compound; then
b. measuring the expression of at least one gene selected from LARGE, HS6ST2 and ST8SIA1, in said samples; and
c. selecting the compounds for which an activation of at least 1.4 fold of the expression of at least one of said genes is measured in the keratinocytes treated in a. as compared to the untreated keratinocytes.

In this second embodiment, the expression of at least one gene selected from LARGE, HS6ST2 and ST8SIA1, measured in the sample of keratinocytes not submitted to step a. corresponds to the control value (i.e. untreated keratinocytes).

According to one preferred embodiment, the method comprises a first step a'. of preparing samples of keratinocytes. Thus, preferably, the present invention relates to an in vitro method for screening for candidate compounds for preventing and/or attenuating ageing of the skin, and/or for hydrating the skin, comprising the following steps:
a'. preparing at least two samples of keratinocytes;
a. bringing one of the samples into contact with at least one test compound; then
b. measuring the expression of at least one gene selected from LARGE, HS6ST2 and ST8SIA1, in said samples; and
c. selecting the compounds for which an activation of at least 1.6 fold of the expression of at least one of said genes is measured in the keratinocytes treated in a. as compared to the untreated keratinocytes.

In this second embodiment, the expression of at least one gene selected from LARGE, HS6ST2 and ST8SIA1, measured in the sample of keratinocytes not submitted to step a. corresponds to the control value (i.e. untreated keratinocytes).

DETAILED DESCRIPTION OF THE INVENTION

By the expression "ageing of the skin" is intended any change in the external appearance of the skin due to ageing, preferably due to photo-induced ageing or photo-aging, such as, for example, wrinkles and fine lines, withered skin, flaccid skin, thinned skin, and skin lacking elasticity and/or tonus, and also any internal change in the skin which is not systematically reflected by a changed external appearance, such as, for example, any internal degradation of the skin, particularly of collagen, following exposure to ultraviolet radiation.

By "hydrating the skin", it is meant maintaining the natural humidity of the skin and preventing its drying, notably by improving skin cell communication and function, including improving its barrier function.

The test compounds may be of any type. They may be of natural origin or may have been produced by chemical synthesis. This may involve a library of structurally defined chemical compounds, uncharacterized compounds or substances, or a mixture of compounds.

Natural compounds include compounds from animal or vegetal origin, like plants. Preferably, the test compounds are vegetal, preferably chosen from botanical extracts.

According to step a., the test compound is put into contact with a sample of keratinocytes.

According to step b., the expression of at least one gene selected from LARGE, HS6ST2 and ST8SIA1 is measured in said keratinocytes. Preferably, the expression of the LARGE gene is measured in step b.

Indeed, surprisingly, the Applicant shows that LARGE gene expression is decreased with UVB irradiation. UVB irradiation is a factor which is well known for aggravating aging, and dehydration. Therefore, without being bound by any theory, abnormal glycosylation due to LARGE gene expression decrease may worsen during skin aging. This may be corrected by the administration of the compound(s) identified according to the invention.

The term "expression of at least one gene selected from LARGE, HS6ST2 and ST8SIA1" is intended to mean the mRNA of the corresponding gene, or the protein encoded by the corresponding gene. Said gene expression may thus be measured by quantifying the mRNA or the protein. This is notably shown in examples 4, 5 and 12.

Those skilled in the art are familiar with the techniques for quantitatively or semi-quantitatively detecting the mRNA of the gene of interest, and thus, determining said gene expression. Techniques based on hybridization of the mRNA with specific nucleotide probes are the most common, like Northern blotting, RT-PCR (reverse transcriptase polymerase chain reaction), quantitative RT-PCR (qRT-PCR).

The expression of at least one gene selected from LARGE, HS6ST2 and ST8SIA1 after treatment with the test compound is then compared to a control value, i.e. a value obtained in the same keratinocytes before treatment, or a value obtained in another sample of keratinocytes which are untreated.

According to step c., the useful compounds are those for which an activation of at least 1.4 fold of the expression of at least one of said genes is measured in the keratinocytes treated in a. as compared to the untreated keratinocytes. Preferably, the activation of the expression of at least one of said genes is of at least 2 fold.

In one preferred embodiment, according to step c., the useful compounds are those for which an activation of at least 1.6 fold of the expression of at least one of said genes is measured in the keratinocytes treated in a. as compared to the untreated keratinocytes. Preferably, the activation of the expression of at least one of said genes is of at least 2 fold.

The compounds selected by means of the screening methods defined herein can subsequently be tested on other in vitro models and/or in vivo models (in animals or humans) for their effects on skin ageing and/or skin hydration. The useful compounds according to the invention are activators of the targeted LARGE, HS6ST2 and/or ST8SIA1 genes.

A subject of the invention is also the cosmetic use of an activator of the expression of at least one gene selected from LARGE, HS6ST2 and ST8SIA1, which can be obtained according to the above described method, for preventing and/or attenuating ageing of the skin and/or for hydrating the skin.

According to another aspect, an objet of the present invention is the use of at least one activator of the expression of at least one gene selected from LARGE, HS6ST2 and ST8SIA1, which can be obtained according to the above described method, to make a therapeutic composition for preventing and/or attenuating ageing of the skin and/or for hydrating the skin. The present invention thus also relates to the use of at least one activator of the expression of at least one gene selected from LARGE, HS6ST2 and ST8SIA1, which can be obtained according to the above described method, for preventing and/or attenuating ageing of the skin and/or for hydrating the skin.

The activator refers to a compound which substantially increases the expression of at least one gene selected from LARGE, HS6ST2 and ST8SIA1, i.e. the quantity of at least one mRNA or protein encoded by at least one of the corresponding genes. The term "substantially" means an increase of at least 1.4 fold, preferably at least 1.6 fold, and more preferably of at least 2 fold.

The activator can be used in a proportion of from 0.001 to 10% by weight, preferably in a proportion of from 0.01 to 5% by weight of the composition.

The activator may be chosen from organic molecules, but may also be a botanical extract.

The activators identified thanks to the screening method described above can be formulated within a composition, in combination with a physiologically acceptable carrier, preferably a cosmetically acceptable medium, i.e. a medium that is suitable for use in contact with human skin without any risk of toxicity, incompatibility, instability or allergic response and especially that does not cause any sensations of discomfort (redness, tautness, stinging, etc.) that are unacceptable to the user. These compositions may be administered, for example, orally, or topically. Preferably, the composition is applied topically. By oral administration, the composition may be in the form of tablets, gel capsules, sugar-coated tablets, syrups, suspensions, solutions, powders, granules, emulsions, suspensions of microspheres or nanospheres or lipid or polymeric vesicles for controlled release. By topical administration, the composition is more particularly for use in treating the skin and may be in the form of salves, creams, milks, ointments, powders, impregnated pads, solutions, gels, sprays, lotions or suspensions. It may also be in the form of suspensions of microspheres or nanospheres or lipid or polymeric vesicles or polymeric patches or hydrogels for controlled release. This composition for topical application may be in anhydrous form, in aqueous form or in the form of an emulsion. The composition for topical application may be in the form of an oil-in-water, water-in-oil or multiple emulsion (W/O/W or O/W/O), which may optionally be microemulsions or nanoemulsions, or in the form of an aqueous dispersion, a solution, an aqueous gel or a powder. In a preferred variant, the composition is in the form of a gel, a cream or a lotion.

The physiologically acceptable carrier of the composition generally comprises water and optionally other solvents such as ethanol.

This composition is preferably used as a care and/or cleansing product for facial and/or bodily skin and it may especially be in the form of a fluid, a gel or a mousse, conditioned, for example, in a pump-dispenser bottle, an aerosol or a tube, or in the form of cream conditioned, for example, in a jar. As a variant, it may be in the form of a makeup product and in particular a foundation or a loose or compact powder.

It may comprise various adjuvants, such as at least one compound chosen from:

oils, which may be chosen especially from: linear or cyclic, volatile or non-volatile silicone oils, such as polydimethylsiloxanes (dimethicones), polyalkylcyclosiloxanes (cyclomethicones) and polyalkylphenylsiloxanes (phenyl dimethicones); synthetic oils such as fluoro oils, alkylbenzoates and branched hydrocarbons such as polyisobutylene; plant oils and especially soybean oil or jojoba oil; and mineral oils such as liquid petroleum jelly;

waxes such as ozokerite, polyethylene wax, beeswax or carnauba wax;

silicone elastomers obtained especially by reaction, in the presence of a catalyst, of a polysiloxane containing at least one reactive group (especially hydrogen or vinyl) and bearing at least one alkyl group (especially methyl) or phenyl, in a terminal and/or side position, with an organosilicone such as an organohydrogenopolysiloxane;

surfactants, preferably emulsifying surfactants, whether they are nonionic, anionic, cationic or amphoteric, and in particular fatty acid esters of polyols such as fatty acid esters of glycerol, fatty acid esters of sorbitan, fatty acid esters of polyethylene glycol and fatty acid esters of sucrose; fatty alkyl ethers of polyethylene glycol; alkylpolyglucosides; polysiloxane-modified polyethers; betaine and derivatives thereof; polyquaterniums; ethoxylated fatty alkyl sulfate salts; sulfosuccinates; sarcosinates; alkyl and dialkyl phosphates, and salts thereof; and fatty acid soaps;

co-surfactants such as linear fatty alcohols and in particular cetyl alcohol and stearyl alcohol;

thickeners and/or gelling agents, and in particular crosslinked or non-crosslinked, hydrophilic or amphiphilic homopolymers and copolymers, of acryloylmethylpropanesulfonic acid (AMPS) and/or of acrylamide and/or of acrylic acid and/or of acrylic acid salts or esters; xanthan gum or guar gum; cellulose derivatives; and silicone gums (dimethiconol);

organic screening agents, such as dibenzoylmethane derivatives (including butylmethoxydibenzoylmethane), cinnamic acid derivatives (including ethylhexyl methoxycinnamate), salicylates, para-aminobenzoic acids, β,β'-diphenyl acrylates, benzophenones, benzylidenecamphor derivatives, phenylbenzimidazoles, triazines, phenylbenzotriazoles and anthranilic derivatives;

inorganic screening agents, based on mineral oxides in the form of coated or uncoated pigments or nanopigments, and in particular based on titanium dioxide or zinc oxide;

dyes;

preserving agents;

sequestrants such as EDTA salts;

fragrances;

and mixtures thereof, without this list being limiting.

Examples of such adjuvants are especially mentioned in the CTFA dictionary (International Cosmetic Ingredient Dictionary and Handbook published by The Cosmetic, Toiletry and Fragrance Association, 11th edition, 2006), which describes a wide variety, without limitation, of cosmetic and pharmaceutical ingredients usually used in the skincare industry, that are suitable for use as additional ingredients in the compositions according to the present invention.

The composition may also comprise at least one compound with an optical effect such as fillers, pigments, nacres, tensioning agents and matting polymers, and mixtures thereof.

The term "fillers" should be understood as meaning colorless or white, mineral or synthetic, lamellar or non-lamellar particles suitable for giving the composition body or rigidity and/or softness, a matt effect and uniformity immediately on application. Fillers that may especially be mentioned include talc, mica, silica, kaolin, Nylon® powders such as Nylon-12 (Orgasol® sold by the company Atochem), polyethylene powders, polyurethane powders, polystyrene powders, polyester powders, optionally modified starch, silicone resin microbeads such as those sold by the company Toshiba under the name Tospearl®, hydroxyapatite, and hollow silica microspheres (Silica Beads® from the company Maprecos).

The term "pigments" should be understood as meaning white or colored, mineral or organic particles that are insoluble in the medium, which are intended to color and/or opacify the composition. They may be of standard or nanometric size. Among the mineral pigments that may be mentioned are titanium dioxide, zirconium dioxide and cerium dioxide, and also zinc oxide, iron oxide and chromium oxide.

The term "nacres" should be understood as meaning iridescent particles that reflect light. Among the nacres that may be envisaged, mention may be made of natural mother-of-pearl, mica coated with titanium oxide, with iron oxide, with natural pigment or with bismuth oxychoride, and also colored titanium mica.

The mass concentration in the aqueous phase of these fillers and/or pigments and/or nacres is generally from 0.1% to 20% and preferably from 0.2% to 7% by weight relative to the total weight of the composition.

The term "tensioning agent" should be understood as meaning a compound suitable for making the skin taut and, by means of this tension effect, making the skin smooth and reducing or even immediately eliminating wrinkles and fine lines therefrom. Tensioning agents that may be mentioned include polymers of natural origin. The term "polymer of natural origin" means polymers of plant origin, polymers derived from integuments, egg proteins and lattices of natural origin. These polymers are preferably hydrophilic. Polymers of plant origin that may especially be mentioned include proteins and protein hydrolyzates, and more particularly extracts of cereals, of legumes and of oil-yielding plants, such as extracts of corn, of rye, of wheat, of buckwheat, of sesame, of spelt, of pea, of bean, of lentil, of soybean and of lupin. The synthetic polymers are generally in the form of a latex or a pseudolatex and may be of polycondensate type or obtained by free-radical polymerization. Mention may be made especially of polyester/polyurethane and polyether/polyurethane dispersions. Preferably, the tensioning agent is a copolymer of PVP/dimethiconyl acrylate and of hydrophilic polyurethane (Aquamere S-2001® from the company Hydromer).

The term "matting polymers" means herein any polymer in solution, in dispersion or in the form of particles, which reduces the sheen of the skin and which unifies the complexion. Examples that may be mentioned include silicone elastomers; resin particles; and mixtures thereof. Examples of silicone elastomers that may be mentioned include the products sold under the name KSG® by the company Shin-Etsu, under the name Trefil®, BY29® or EPSX® by the company Dow Corning or under the name Gransil® by the company Grant Industries.

The composition used according to the invention may also comprise active agents other than the activator, and in particular at least one active agent chosen from: agents that stimulate the production of growth factors; anti-glycation or deglycating agents; agents that increase collagen synthesis or that prevent its degradation (anti-collagenase agents and especially matrix metalloprotease inhibitors); agents that increase elastin synthesis or prevent its degradation (anti-elastase agents); agents that stimulate the synthesis of integrin or of focal adhesion constituents such as tensin; agents that increase the synthesis of glycosaminoglycans or proteoglycans or that prevent their degradation (anti-proteoglycanase agents); agents that increase fibroblast proliferation; depigmenting or anti-pigmenting agents; antioxidants or free-radical scavengers or anti-pollution agents; and mixtures thereof, without this list being limiting.

Examples of such agents are especially: plant extracts and in particular extracts of *Chondrus crispus*, of *Thermus thermophilus*, of *Pisum sativum* (Proteasyl® TP LS), of *Centella asiatica*, of *Scenedesmus*, of *Moringa pterygosperma*, of witch hazel, of *Castanea sativa*, of *Hibiscus sabdriffa*, of *Polianthes tuberosa*, of *Argania spinosa*, of *Aloe vera*, of *Narcissus tarzetta*, or of liquorice; an essential oil of *Citrus aurantium* (Neroli); α-hydroxy acids such as glycolic acid, lactic acid and citric acid, and esters thereof; β-hydroxy acids such as salicylic acid and derivatives thereof; plant protein hydrolyzates (especially of soybean or of hazelnut); acylated oligopeptides (sold especially by the company Sederma under the trade names Maxilip®, Matrixyl® 3000, Biopeptide® CL or Biopeptide® EL); yeast extracts and in particular of *Saccharomyces cerevisiae*; algal extracts and in particular of laminairia; vitamins and derivatives thereof such as retinyl palmitate, ascorbic acid, ascorbyl glucoside, magnesium or sodium ascorbyl phosphate, ascorbyl palmitate, ascorbyl tetraisopalmitate, ascorbyl sorbate, tocopherol, tocopheryl acetate and tocopheryl sorbate; arbutin; kojic acid; ellagic acid; and mixtures thereof.

As a variant or in addition, the composition used according to the invention may comprise at least one elastase inhibitor (anti-elastase), such as an extract of *Pisum sativum* seeds that is sold especially by the company Laboratoires Sérobiologiques/Cognis France under the trade name Proteasyl TP LS®.

The composition may also contain inert additives or combinations of these additives, such as wetting agents, stabilizers, moisture regulators, pH regulators, osmotic pressure modifiers, or UV-A and UV-B screens.

The following examples illustrate the invention without limiting the scope thereof.

EXAMPLES

Example 1

Test of the Expression of LARGE in Human Keratinocytes

Protocol:

The expression of the messenger RNA (mRNA) of LARGE was evaluated in cultured human keratinocytes by PCR and the expression of the LARGE protein was evaluated in human skin samples by immunohistochemical staining.

Keratinocytes derived from neonatal foreskins (Cascade Biologics/Invitrogen, Portland, Oreg., USA) were placed in 6-well plates and cultured in keratinocyte growth culture medium with supplement (EpiLife, Invitrogen). After culturing for 24 hours in an incubator at 37° C., the medium was changed for basal medium and cultured for additional 24 hours, the 70% confluent cells were washed with PBS buffer (Invitrogen) and then used for mRNA extraction.

The mRNA was isolated using the Qiagen RNeasy kit (Qiagen, CA) and quantified using the QuantIt kit (Invitrogen, CA).

Reverse transcription was performed using the gene Amp RNA PCR kit (Invitrogen) according to the manufacturer's recommendations.

To quantify the expression level of the mRNA of LARGE in cultured keratinocytes, real-time reverse transcription polymerase chain reaction (QRT-PCR) was used. The results were normalized relative to the expression of housekeeping genes of these samples. The results were expressed in terms of the number of times of change of expression level of the target gene LARGE.

The LARGE PCR primers (Fujimura et al, 2005) were obtained from Invitrogen (Invitrogen, CA).

Housekeeping gene was PBGD. The PBGD PCR primers were obtained from Invitrogen (Invitrogen, CA).

Real-time-PCR was performed (Biorad iCyclerIQ) using SYBR Green I detection. In all the tests, the cDNA was amplified using a standardized program. Each sample was loaded with IQ SYBR green supermix, $H_2O$, and each primer. The final amount of cDNA per reaction corresponded to 75 ng of total RNA used for reverse transcription.

The relative quantification of the expression of the target gene was performed using the Pfaffl mathematical model (Pfaffl, M W, Nucleic Acids Res. 29(9), p. E45, 2001). The results were confirmed using cells from two different donors.

The expression of the LARGE protein was evaluated by immunohistochemistry (IHC), on frozen skin samples from different donors (ZenBio Inc. NC, USA and Cybrdi, MD, USA). Staining was performed on 6 µm sections with primary anti-human LARGE goat antibodies (Santa Cruz Biotechnology, CA, USA) and secondary donkey anti-goat antibodies (Rockland Immunochemicals, PA, USA). The staining was visualized using the AEC system (Lab Vision). Staining was assessed on 2-6 sections each from 3-5 donors.

Results:

Evaluation of expression of the LARGE mRNA in keratinocytes from a single donor shows that LARGE is expressed in normal human cultured keratinocytes. The data were confirmed in two donors of keratinocytes.

Evaluation of LARGE staining in human skin showed intense localized staining close to the nucleus in the keratinocytes of the basal, suprabasal, and granular layers of epidermis. The intensity of staining visibly decreased in outer layers of the epidermis.

It emerges from this test that LARGE gene is expressed in normal human keratinocytes in vitro and in vivo.

Example 2

Test of Inhibition of the Expression of the mRNA of LARGE in Normal Human Keratinocytes with UVB Irradiation by Microarray Analysis Protocol:

The effect of UVB irradiation on the expression of the mRNA of LARGE was evaluated in cultured human keratinocytes.

The cytotoxicity of the UVB was evaluated in human cultured keratinocytes before testing the activity. Non-cytotoxic doses of UVB irradiation were used in the experiment.

Keratinocytes derived from neonatal foreskins (Cascade Biologics/Invitrogen, Portland, Oreg., USA) were plated in 6-well plates and cultured in keratinocyte growth culture medium with supplement (EpiLife, Invitrogen). After culturing for 24 hours in an incubator at 37° C., the 40-50% confluent cells were washed with PBS buffer (Invitrogen) and then irradiated with UVB using a BioSun instrument (Vilber Lourmat, France) with different doses of UVB and finally incubated for 24 hours in keratinocyte basal culture medium (EpiLife, Invitrogen). The 70-80% confluent cells were washed with PBS buffer (Invitrogen) and quick-frozen cell pellets were prepared for mRNA extraction and microarray analysis.

To quantify the expression level of the mRNA of LARGE in keratinocyte samples, Agilent Whole Human Genome Oligo Microarray Analysis was used. The results for the LARGE expression in UVB-irradiated samples were normalized relative to the expression of LARGE in control non-irradiated samples. The results were expressed in terms of the number of times of change of expression level of the target gene LARGE. The results were confirmed using cells from two different donors.

The mRNA was isolated using the standard RNA extraction protocols (NucleoSpin® RNA II, Macherey-Nagel). Quality of RNA samples were checked via the Agilent 2100 Bioanalyzer platform (Agilent Technologies, Palo Alto, USA). The RNA Integrity Number was evaluated to check integrity and overall quality of total RNA samples.

To produce Cy3- and Cy5-labeled cRNAs, the RNA samples were amplified and labeled using the Agilent Low RNA Input Linear Amp Kit (Agilent Technologies, Palo Alto, USA) following the manufacturer's protocol.

The hybridization procedure was performed according to the Agilent 60-mer oligo microarray processing protocol using the Agilent Gene Expression Hybridization Kit (Agilent Technologies, Palo Alto, USA).

Fluorescence signals of the hybridized Agilent Oligo Microarrays were detected using Agilent's DNA microarray scanner (Agilent, Palo Alto, USA). The Agilent Feature Extraction Software was used to read out and process the microarray image files.

For determination of differential gene expression, data files were further analyzed using the Rosetta Resolverá gene expression data analysis system (Rosetta Biosoftware). Genes with a fold change >2 and p-value <0.01 were considered as differentially expressed.

Results:

Evaluation of fold change in expression of the LARGE mRNA in keratinocytes from a single donor, irradiated with the doses of UVB 20 mJ/cm$^2$ compare to non-irradiated control was −4.0 (±0.00) and −4.5 (±0.00).

Evaluation of fold change in expression of the LARGE mRNA in keratinocytes from a single donor, irradiated with the doses of UVB 30mJ/cm$^2$ compare to non-irradiated control was −6.6 (±0.00) and −7.9 (±0.00).

The data were confirmed in two donors of keratinocytes.

It emerges from this test that UVB irradiation significantly decreases LARGE gene expression in normal human keratinocytes.

Example 3

Test of Inhibition of the Expression of the mRNA of LARGE in Normal Human Keratinocytes with UVB Irradiation by PCR Protocol:

The effect of UVB irradiation on the expression of the mRNA of LARGE was evaluated on cultured keratinocytes by PCR.

Keratinocytes derived from neonatal foreskins (Cascade Biologics/Invitrogen, Portland, Oreg., USA) were plated in 6-well plates and cultured in keratinocyte growth culture medium with supplement (EpiLife, Invitrogen). After culturing for 24 hours in an incubator at 37° C., the 40-50% confluent cells were washed with PBS buffer (Invitrogen) and then irradiated with UVB using a BioSun instrument (Vilber Lourmat, France) with different doses of UVB and finally incubated for 24 hours in keratinocyte basal culture medium (EpiLife, Invitrogen). The 70-80% confluent cells were washed with PBS buffer (Invitrogen) and used for mRNA extraction.

A test similar to that of Example 1 was performed.

The results were confirmed using cells from two different donors. The cytotoxicity of the UVB was evaluated in human cultured keratinocytes before testing the activity.

Results:

Evaluation of expression of the LARGE mRNA in keratinocytes from a single donor, irradiated with the doses of UVB 10 mJ/cm$^2$·20 mJ/cm$^2$, and 30 mJ/cm$^2$ was 0.28 (±0.03), 0.13 (±0.04), and 0.06 (±0.01), respectively. In non-treated control keratinocytes expression level was 1.0 (±0.20). The data were confirmed in two donors of keratinocytes.

It emerges from this test that UVB irradiation significantly decreases LARGE gene expression in normal human keratinocytes.

Example 4

Test of Stimulation of the Expression of the mRNA of LARGE in Normal Human Keratinocytes with an Active Agent Protocol:

The effect of Resveratrol, on the expression of the mRNA of LARGE was evaluated in cultured keratinocytes by PCR.

Keratinocytes derived from neonatal foreskins (Invitrogen, CA, USA) were cultured in 6-well plates in keratinocyte culture medium with supplement (EpiLife, Invitrogen). After culturing for 24 hours at 37° C., the 70% confluent cells were washed with PBS buffer (Invitrogen, CA) and incubated with basal keratinocytes culture medium (EpiLife, Invitrogen) containing the active agent to be tested, for 24 hours, at increasing concentrations. The cytotoxicity of the active agent was evaluated in human cultured keratinocytes before testing the activity.

A test similar to that of Example 1 was performed.

Results:

Evaluation of LARGE mRNA expression in keratinocytes treated with 0.002%, 0.001%, and 0.0005% Resveratrol was 4.84 (±0.94), 3.63 (±0.41), and 2.7 (±0.13), respectively. In control non-treated keratinocytes evaluation of LARGE mRNA expression was 0.99 (±0.01). This demonstrates that the LARGE mRNA expression is significantly increased with Resveratrol treatments. The data were confirmed in two donors of keratinocytes.

The results are given in Table 1 below:

TABLE 1

|  | Concentration[1] | Stimulation of LARGE mRNA[2] | Standard deviation |
|---|---|---|---|
| Untreated keratinocytes | — | 0.99 | 0.01 |
| Resveratrol | 0.002% | 4.84 | 0.94 |
|  | 0.001% | 3.63 | 0.41 |
|  | 0.0005% | 2.70 | 0.13 |

[1]the concentration of the active agent is expressed as the weight of active agent per weight of preparation
[2]the degree of stimulation is somewhat overestimated due to the effect on housekeeping gene expression It emerges from this test that the active agent tested makes it possible to significantly stimulate the expression of mRNA of LARGE in normal human keratinocytes.

Example 5

Test of Stimulation of the Expression of LARGE Protein in Normal Human Keratinocytes with a Resveratrol Protocol:

The effect of the Resveratrol used in Example 4 on the expression of the LARGE protein was evaluated in cultured keratinocytes.

Keratinocytes derived from neonatal foreskin (Invitrogen, CA, USA) were cultivated in 6-well plates containing cover glasses coated with poly-L-ornithine (Sigma, MO) in keratinocyte culture medium with supplement (EpiLife, Invitrogen). After culturing for 24 hours at 37° C., the 40-50% confluent cells were washed with PBS buffer (Invitrogen, CA) and incubated with basal keratinocytes culture medium (EpiLife, Invitrogen) containing the extract to be tested, for 48 hours. The cytotoxicity of the extract was evaluated in human cultured keratinocytes before testing the activity.

To quantify the expression of the LARGE protein in a treated sample relative to an untreated sample, immunocytochemical staining (ICC) of cover glasses with cultured keratinocytes was used. Staining was performed in triplicates, with primary goat anti-human LARGE antibodies (Santa Cruz, Calif.) and secondary donkey anti-goat antibodies (Rockland Immunochemicals, PA). The staining was visualized with AEC system (Lab Vision Corporation, CA). The extent of staining was assessed on thirty random images for each experimental condition, and a visual assessment of the staining was made using a scale from 1 to 5, with 1 being the least intense and 5 being the most intense. The significance of the difference between mean values was assessed using unpaired t test.

Results:

Evaluation of LARGE staining in keratinocytes treated with 0.002% Resveratrol was 3.8 (±0.93), in keratinocytes treated with 0.001% Resveratrol it was 2.67 (±0.55), in keratinocytes treated with 0.0005% Resveratrol it was 2.7 (±0.88) and in non-treated control keratinocytes it was 2.03 (±0.72). The difference of LARGE staining in untreated and treated keratinocytes was significant ($p<0.005$). This demonstrates that the amount of LARGE protein is significantly increased with Resveratrol treatments. The data presented are from one donor of keratinocytes.

The results are given in Table 2 below:

TABLE 2

|  | Concentration[1] | Stimulation of LARGE protein | Standard deviation |
|---|---|---|---|
| Untreated keratinocytes | — | 2.03 | 0.72 |
| Resveratrol | 0.002% | 3.80 | 0.93 |
|  | 0.001% | 2.67 | 0.55 |
|  | 0.0005% | 2.70 | 0.88 |

[1]the concentration of the extract is expressed as the weight of crude extract per weight of preparation.

It emerges from this test that Resveratrol make it possible to stimulate the expression of LARGE protein in normal human keratinocytes.

Example 6

Test of the Expression of HS6ST2 in Human Keratinocytes

Protocol:

The expression of the mRNA of HS6ST2 was evaluated in cultured human keratinocytes by PCR.

Keratinocytes derived from neonatal foreskins (Cascade Biologics/Invitrogen, Portland, Oreg., USA) were placed in 6-well plates and cultured in keratinocyte growth culture medium with supplement (EpiLife, Invitrogen). After culturing for 24 hours in an incubator at 37° C., the medium was changed for basal medium and cultured for additional 24 hours, the 70% confluent cells were washed with PBS buffer (Invitrogen) and then used for mRNA extraction.

The mRNA was isolated using the Qiagen RNeasy kit and quantified using the QuantIt kit (Invitrogen, CA).

To quantify the expression level of the mRNA of HS6ST2 in cell samples, real-time reverse transcription polymerase chain reaction (RT-PCR) was used. The results were normalized relative to the expression of housekeeping genes of these samples. The results were expressed in terms of the number of times of change of expression level of the target gene HS6ST2 in keratinocytes.

The HS6ST2 PCR primers were obtained from Invitrogen (Invitrogen, CA).

Housekeeping gene was B2M. The B2M PCR primers were obtained from Invitrogen (Invitrogen, CA).

Reverse transcription was performed using the gene Amp RNA PCR kit (Applied Biosystems) according to the manufacturer's recommendations.

The real-time PCR measurement was performed using the iCYCLER IQ machine (Bio-rad, CA) with Taqman probes.

In all the tests, the cDNA was amplified using a standardized program. Each sample was charged with Taqman master-mix, Taqman probes, and water. The final amount of cDNA per reaction corresponded to 75 ng of total RNA used for the reverse transcription.

The relative quantification of the expression of the target gene was performed using the Pfaffl mathematical model (Pfaffl, M W, Nucleic Acids Res. 29(9), p. E45, 2001).

Results:

Evaluation of expression of the HS6ST2 mRNA in keratinocytes from a single donor shows that HS6ST2 is expressed in normal human cultured keratinocytes.

Example 7

Test of Inhibition of the Expression of the mRNA of the HS6ST2 in Normal Human Keratinocytes with UVB Irradiation by Microarray Analysis Protocol:

The effect of UVB irradiation on the expression of the mRNA of HS6ST2 was evaluated in cultured human keratinocytes.

The cytotoxicity of the UVB was evaluated in human cultured keratinocytes before testing the activity. Non-cytotoxic dose of UVB irradiation were used in the experiment.

A test similar to that of Example 2 was performed. The results were confirmed using cells from two different donors.

Results:

Evaluation of fold change in expression of the HS6ST2 mRNA in keratinocytes from a single donor, irradiated with the doses of UVB 20 mJ/cm$^2$ compare to non-irradiated control was −3.71 (±0.00) and −3.67 (±0.00).

Evaluation of fold change in expression of the HS6ST2 mRNA in keratinocytes from a single donor, irradiated with the doses of UVB 30 mJ/cm$^2$ compare to non-irradiated control was −8.83 (±0.00) and −11.47 (±0.00). The data were confirmed in two donors of keratinocytes.

It emerges from this test that UVB irradiation significantly decreases HS6ST2 mRNA expression in normal human keratinocytes.

Example 8

Test of Inhibition of the Expression of the mRNA of the HS6ST2 in Normal Human Keratinocytes with UVB Irradiation by PCR Protocol:

The effect of UVB irradiation on the expression of the mRNA of HS6ST2 was evaluated on cultured keratinocytes by PCR.

Keratinocytes derived from neonatal foreskins (Cascade Biologics/Invitrogen, Portland, Oreg., USA) were placed in 6-well plates and cultured in keratinocyte growth culture medium with supplement (EpiLife, Invitrogen). After culturing for 24 hours in an incubator at 37° C., the 40-50% confluent cells were washed with PBS buffer (Invitrogen) and then irradiated with UVB using a BioSun instrument (Vilber Lourmat, France) with different doses of UVB and finally incubated for 24 hours in keratinocyte basal culture medium (EpiLife, Invitrogen). The 70-80% confluent cells were washed with PBS buffer (Invitrogen) and used for mRNA extraction.

The positive results were confirmed using cells from two different donors. The cytotoxicity of the UVB was evaluated in human cultured keratinocytes before testing the activity.

A test similar to that of Example 6 was performed. The results were confirmed using cells from two different donors.

Results:

Evaluation of expression of the HS6ST2 mRNA in keratinocytes from a single donor, irradiated with the doses of UVB 10 mJ/cm$^2$, 20 mJ/cm$^2$, and 30 mJ/cm$^2$ was 0.62 (±0.08), 0.22 (±0.06), and 0.17 (±0.06), respectively. In non-treated control keratinocytes expression level was 1.0 (±0.04). The data were confirmed in two donors of keratinocytes.

It emerges from this test that UVB irradiation significantly decreases HS6ST2 mRNA expression in normal human keratinocytes.

Example 9

Test of Stimulation of the Expression of the Messenger RNA (mRNA) of HS6ST2 in Normal Human Keratinocytes with an Active Agent Protocol:

The effect of Resveratrol, on the expression of the mRNA of HS6ST2 was evaluated in cultured keratinocytes by PCR. A test similar to that of Example 7 was performed.

Keratinocytes derived from neonatal foreskins (Invitrogen, CA, USA) were cultured in 6-well plates in keratinocyte culture medium with supplement (EpiLife, Invitrogen). After culturing for 24 hours at 37° C., the 70% confluent cells were washed with PBS buffer (Invitrogen, CA) and incubated with basal keratinocytes culture medium (EpiLife, Invitrogen) containing the active agent to be tested, for 24 hours, at increasing concentrations. The cytotoxicity of the active agent was evaluated in human cultured keratinocytes before testing the activity.

Keratinocytes were treated with various concentrations of the active agent for 24 hours. The mRNA was isolated using the Qiagen RNeasy kit (Qiagen, CA) and quantified using the QuantIt kit (Invitrogen, CA).

Results:

Evaluation of HS6ST2 mRNA expression in keratinocytes treated with 0.00125% and 0.00006% Resveratrol was 1.5 (±0.1) and 1.5 (±0.1), respectively. In control non-treated keratinocytes evaluation of HS6ST2 mRNA expression was 1.0 (±0.0). This demonstrates that the HS6ST2 mRNA expression is increased with Resveratrol treatments. The data were confirmed in two donors of keratinocytes.

The results are given in Table 3 below:

TABLE 3

|  | Concentration[1] | Stimulation of HS6ST2 mRNA | Average deviation |
| --- | --- | --- | --- |
| Untreated keratinocytes | — | 1.00 | 0.00 |
| Resveratrol | 0.00125% | 1.49 | 0.04 |
|  | 0.00006% | 1.52 | 0.07 | the concentrations of the active agent is expressed as the weight of active agent per weight of preparation Results are presented as the average of two lots.

It emerges from this test that the active agent tested makes it possible to significantly stimulate the expression of mRNA of HS6ST2 in normal human keratinocytes.

Example 10

Test of the Expression of ST8SIA1 in Human Keratinocytes

Protocol:

The expression of the mRNA of ST8SIA1 was evaluated in cultured human keratinocytes by PCR and the expression of the ST8SIA1 protein was evaluated in human skin samples.

A test similar to that of Example 6 was performed.

The ST8SIA1 PCR primers were obtained from Invitrogen (Invitrogen, CA). Housekeeping gene was B2M. The B2M PCR primers were obtained from Invitrogen (Invitrogen, CA). The results were confirmed using cells from two different donors.

The expression of the ST8SIA1 protein was evaluated by immunohistochemistry (IHC), on frozen skin samples from different donors (ZenBio inc. NC, USA and Cybrdi, MD, USA). Staining was performed on 6 µm sections with primary anti-human ST8SIA1 antibodies (Sigma, MO, USA) and secondary goat anti-rabbit antibodies (Thermo Scientific, CA, USA). The staining was visualized using the AEC system (Thermo Scientific). Staining was assessed on 2-6 sections each from 3-5 donors.

Results:

Evaluation of expression of the ST8SIA1 mRNA in keratinocytes from a single donor showed that ST8SIA1 is expressed in normal human cultured keratinocytes. The data were confirmed in two donors of keratinocytes.

Evaluation of ST8SIA1 staining in human skin showed granular cytoplasmic staining mostly in the keratinocytes of the basal and suprabasal layers of the skin epidermis.

Example 11

Test of Inhibition of the Expression of the mRNA of the ST8SIA1 in Normal Human Keratinocytes with UVB Irradiation by Microarray Analysis Protocol:

The effect of UVB irradiation on the expression of the mRNA of ST8SIA1 was evaluated in cultured human keratinocytes by microarray analysis.

The cytotoxicity of the UVB was evaluated in human cultured keratinocytes before testing the activity. Non-cytotoxic dose of UVB irradiation were used in the experiment.

A test similar to that of Example 2 was performed. The results were confirmed using cells from two different donors.

Results:

Evaluation of fold change in expression of the ST8SIA1 mRNA in keratinocytes from a single donor, irradiated with the doses of UVB 20 mJ/cm$^2$ compare to non-irradiated control was −5.38 (±0.00) and −5.12 (±0.00).

Evaluation of fold change in expression of the ST8SIA1 mRNA in keratinocytes from a single donor, irradiated with the doses of UVB 30 mJ/cm$^2$ compare to non-irradiated control was −7.22 (±0.00) and −11.36 (±0.00). The data were confirmed in two donors of keratinocytes.

It emerges from this test that UVB irradiation significantly decreases ST8SIA1 mRNA expression in normal human keratinocytes.

Example 12

Test of Inhibition of the Expression of the mRNA of the ST8SIA1 in Normal Human Keratinocytes with UVB Irradiation by PCR Protocol:

The effect of UVB irradiation on the expression of the mRNA of ST8SIA1 was evaluated on cultured keratinocytes by PCR.

Keratinocytes derived from neonatal foreskins (Cascade Biologics/Invitrogen, Portland, Oreg., USA) were placed in 6-well plates and cultured in keratinocyte growth culture medium with supplement (EpiLife, Invitrogen). After culturing for 24 hours in an incubator at 37° C., the 40-50% confluent cells were washed with PBS buffer (Invitrogen) and then irradiated with UVB using a BioSun instrument (Vilber Lourmat, France) with different doses of UVB and finally incubated for 24 hours in keratinocyte basal culture medium (EpiLife, Invitrogen). The 70-80% confluent cells were washed with PBS buffer (Invitrogen) and used for mRNA extraction.

The positive results were confirmed using cells from two different donors. The cytotoxicity of the UVB was evaluated in human cultured keratinocytes before testing the activity.

A test similar to that of Example 10 was performed. The results were confirmed using cells from two different donors.

Results:

Evaluation of expression of the ST8SIA1 mRNA in keratinocytes from a single donor, irradiated with the doses of UVB 10 mJ/cm$^2$, 20 mJ/cm$^2$, and 30 mJ/cm$^2$ was 0.48 (±0.09), 0.21 (±0.02), and 0.14 (±0.08), respectively. In non-treated control keratinocytes expression level was 1.01 (±0.17). The data were confirmed in two donors of keratinocytes.

It emerges from this test that UVB irradiation significantly decreases ST8SIA1 mRNA expression in normal human keratinocytes.

Example 13

Test of Stimulation of the Expression of the mRNA of ST8SIA1 in Normal Human Keratinocytes with an Active Agent Protocol:

The effect of Resveratrol, on the expression of the mRNA of ST8SIA1 was evaluated in cultured keratinocytes by PCR.

Keratinocytes derived from neonatal foreskins (Invitrogen, CA, USA) were cultured in 6-well plates in keratinocyte culture medium with supplement (EpiLife, Invitrogen). After culturing for 24 hours at 37° C., the 70% confluent cells were washed with PBS buffer (Invitrogen, CA) and incubated with basal keratinocytes culture medium (EpiLife, Invitrogen) containing the active agent to be tested, for 24 hours, at increasing concentrations. The cytotoxicity of the active agent was evaluated in human cultured keratinocytes before testing the activity.

A test similar to that of Example 10 was performed. The results were confirmed using cells from two different donors.

Results:

Evaluation of ST8SIA1 mRNA expression in keratinocytes treated with 0.00025%, 0.000125%, and 0.00006% Resveratrol was 1.33 (±0.18), 1.62 (±0.02), and 1.25 (±0.23), respectively. In control non-treated keratinocytes evaluation of ST8SIA1 mRNA expression was 1.01 (±0.01). This demonstrates that the ST8SIA1 mRNA expression is increased with Resveratrol treatments. The data were confirmed in two donors of keratinocytes. Results are presented as the average of two lots.

The results are given in Table 4 below:

TABLE 4

|  | Concentration[1] | Stimulation of ST8SIA1 mRNA | Standard deviation |
|---|---|---|---|
| Untreated keratinocytes | — | 1.01 | 0.01 |
| Resveratrol | 0.00025% | 1.33 | 0.18 |
|  | 0.000125% | 1.62 | 0.02 |
|  | 0.00006% | 1.25 | 0.23 |

[1] the concentration of the active agent is expressed as the weight of active agent per weight of preparation It emerges from this test that the active agent tested makes it possible to significantly stimulate the expression of mRNA of ST8SIA1 in normal human keratinocytes.

Example 14

Cosmetic Composition (O/W Serum)

The following composition may be prepared in a classical manner for the man skilled in the art.

| INCI name | % (w/w) |
|---|---|
| Water | QSP 100,00 |
| Chelating agent | 0.05 |
| pH balance | 0.05 |
| Preservatives | 0.05 |
| Glycol | 3.25 |
| AMMONIUM ACRYLOYLDIMETHYLTAURATE/ VP COPOLYMER | 1.20 |
| ACRYLATES/C10-30 ALKYL ACRYLATE CROSSPOLYMER | 0.20 |
| GLYCERIN | 3.00 |
| GLYCERYLPOLYMETHACRYLATE | 4.18 |
| SODIUM ACETYLATED HYALURONATE | 0.05 |
| Oil | 10.00 |
| ALCOHOL | 8.00 |
| PERFUMES | 0.30 |
| Resveratrol | 0.05 |

The invention claimed is:

1. A method for screening for candidate compounds that increase the expression level of HS6ST2 in keratinocytes, comprising the following steps:
   (a) bringing at least one test compound in contact with a sample of keratinocytes in vitro;
   (b) measuring the expression of the HS6ST2 gene, in said keratinocytes from step (a); and
   (c) further testing the at least one test compound in an in vitro or in vivo model for its effects on skin aging and/or skin hydration when the expression of the HS6ST2 gene measured in the keratinocytes treated in (a) is increased by at least 1.4 fold compared with the expression level of HS6ST2 in the a sample of untreated keratinocytes.

2. The method according to claim 1, wherein said increase in the expression of the HS6ST2 gene is at least 1.6 fold.

3. The method according to claim 1, wherein the increase in the expression of the HS6ST2 gene is at least 2 fold.

4. The method according to claim 1, wherein step (b) is performed before and after step (a).

5. The method according to claim 1, comprising the following steps:
   (a') preparing two samples of keratinocytes;
   (a) bringing one of said two samples into contact with at least one test compound, and keeping one of the two samples untreated by said at least one test compound;
   (b) measuring the expression of the HS6ST2 gene in said two samples from step (a); and
   (c) further testing the at least one test compound in an in vitro or in vivo model for its effects on skin aging and/or skin hydration when an increase of at least 1.4 fold of the expression of the HS6ST2 gene is measured in the sample of keratinocytes brought into contact with the at least one test compound in step (a) as compared to the sample of untreated keratinocytes.

6. The method according to claim 5, wherein said increase of the expression of the HS6ST2 gene is at least 1.6 fold.

7. The method according to claim 5, wherein said increase of the expression of the HS6ST2 gene is at least 2 fold.

8. The method according to claim 5, wherein step (b) is performed before and after step (a).

9. The method according to claim 5, wherein the expression of the HS6ST2 gene is measured by quantifying the level of HS6ST2 mRNA.

10. The method according to claim 5, wherein the expression of the HS6ST2 gene is measured by quantifying the level of HS6ST2 protein.

11. The method according to claim 5, wherein the at least one test compound is a botanical extract.

12. The method according to claim 1, wherein the expression of the HS6ST2 gene is measured by quantifying the level of HS6ST2 mRNA.

13. The method according to claim 1, wherein the expression of the HS6ST2 gene is measured by quantifying the level of HS6ST2 protein.

14. The method according to claim 1, wherein the at least one test compound is a botanical extract.

15. A method for screening for candidate compounds that increase the expression level of HS6ST2 in keratinocytes, comprising the following steps:
(a) bringing at least one test compound in contact with a sample of keratinocytes in vitro;
(b) measuring the expression of only the HS6ST2 gene, in said keratinocytes from step (a); and
(c) selecting the at least one test compound as a candidate compound when the expression of the HS6ST2 gene measured in the keratinocytes treated in (a) is increased by at least 1.4 fold compared with the expression level of HS6ST2 in a sample of untreated keratinocytes.

16. The method according to claim 15, wherein said increase in the expression of the HS6ST2 gene is at least 1.6 fold.

17. The method according to claim 15, wherein the increase in the expression of the HS6ST2 gene is at least 2 fold.

18. The method according to claim 15, wherein step (b) is performed before and after step (a).

19. The method according to claim 15, comprising the following steps:
(a') preparing two samples of keratinocytes;
(a) bringing one of said two samples into contact with at least one test compound, and keeping one of the two samples untreated by said at least one test compound;
(b) measuring the expression of only the HS6ST2 gene in said two samples from step (a); and
(c) selecting the at least one test compound as a candidate compound when an increase of at least 1.4 fold of the expression of the HS6ST2 gene is measured in the sample of keratinocytes brought into contact with the at least one test compound in step (a) as compared to the sample of untreated keratinocytes.

20. The method according to claim 19, wherein said increase of the expression of the HS6ST2 gene is at least 1.6 fold.

21. The method according to claim 19, wherein said increase of the expression of the HS6ST2 gene is at least 2 fold.

22. The method according to claim 19, wherein step (b) is performed before and after step (a).

23. The method according to claim 19, wherein the expression of the HS6ST2 gene is measured by quantifying the level of HS6ST2 mRNA.

24. The method according to claim 19, wherein the expression of the HS6ST2 gene is measured by quantifying the level of HS6ST2 protein.

25. The method according to claim 19, wherein the at least one test compound is a botanical extract.

26. The method according to claim 15, wherein the expression of the HS6ST2 gene is measured by quantifying the level of HS6ST2 mRNA.

27. The method according to claim 15, wherein the expression of the HS6ST2 gene is measured by quantifying the level of HS6ST2 protein.

28. The method according to claim 15, wherein the at least one test compound is a botanical extract.

* * * * *